United States Patent [19]
Roth

[11] 4,282,873
[45] Aug. 11, 1981

[54] MEDICAL IRRIGATION DEVICE

[76] Inventor: Robert A. Roth, 29 Hyslop Rd., Brookline, Mass. 02146

[21] Appl. No.: 136,890

[22] Filed: Apr. 3, 1980

[51] Int. Cl.³ .............................................. A61M 1/00
[52] U.S. Cl. ................................................ 128/276
[58] Field of Search ............... 128/276, 232, 224, 231, 128/230, 275

[56] References Cited
U.S. PATENT DOCUMENTS

| | | | |
|---|---|---|---|
| 2,487,630 | 11/1949 | Alvarez | 128/232 |
| 2,566,806 | 9/1951 | Miller | 128/276 |
| 3,051,176 | 8/1962 | Alberti | 128/276 |
| 3,926,187 | 12/1975 | Iglasias | 128/232 |

Primary Examiner—John D. Yasko
Attorney, Agent, or Firm—Schiller & Pandiscio

[57] ABSTRACT

A medical irrigation device includes means for connecting a bulb-type syringe to a cannula such as a resectoscope so that fluid may be circulated therethrough in either direction and selectively either by a direct path therebetween or by a circuitous path including a specimen collecting receptacle whereby lavage may be accomplished with rapid reversal of fluid flow direction yet with periodic removal of particulate matter from the circulating fluid.

5 Claims, 3 Drawing Figures

MEDICAL IRRIGATION DEVICE

BACKGROUND OF THE INVENTION

This invention relates to apparatus for use in medical proceedures, and more particularly to irrigation apparatus in which the direction of fluid flow may be rapidly reversed and particulate matter in the circulating fluid may be rapidly removed, thereby facilitating lavage.

Medical irrigation devices are well-known, and are particularly used in urology for lavage in a variety of procedures, such as the treatment of chronic infections, the cleansing of the inspection field prior to cystoscopy, and the post-operative treatment of the urinary bladder.

A common prior art device widely utilized for irrigation of the urinary bladder is the so-called Ellik evacuator. This device comprises a unitary body, typically of glass, forming a pair of hollow chambers the interiors of which directly communicate with one another through a short restricted passageway. One of the chambers is further provided with a pair of conduits communicating with its interior, one of such conduits being provided with means for connecting it with a cannula, such as a resectoscope or similar device, and the other conduit being adapted to be connected to a bulb-type syringe. In use, the syringe and both chambers of the Ellik evacuator are filled with a suitable sterile fluid, and the resectoscope or like catheter is introduced into the urinary bladder or other body cavity to be irrigated. Compression of the syringe then introduces the fluid into the body cavity, and expansion of the syringe withdraws it. If the evacuator is held such that the chamber having the conduits communicating with the syringe and the resectoscope is uppermost, then particulate matter carried by the fluid stream into the evacuator during the expansion of the syringe, may settle by gravity into the lower chamber, provided of course that the density of the particles is greater than that of the fluid. Once the particulate matter has settled into the lower chamber, the restricted passageway between the two chambers acts to minimize this material from being agitated by, and drawn again into, the flow stream passing through the upper chamber, between syringe and catheter.

A disadvantage of the Ellik evacuator is the slow rate of precipitation of the particulate matter, much of which has a density not unlike that of water. As a consequence, if the syringe is rapidly and cyclically compressed and expanded in order to produce vigorous agitation during lavage, a large percentage of the particulate matter evacuated during the expansion of the syringe will remain in suspension in the upper chamber and be re-introduced into the body cavity during the next compression cycle of the syringe, or alternatively be drawn into the syringe and trapped therein. Even if vigorous agitation is not desired, the use of gravity to effect separation of the debris from the fluid results in a time-consuming lavage procedure. A further disadvantage of the Ellik evacuator is that, in order to subject to laboratory examination the particulate matter collected in the evacuator, it is necessary to remove the material collected in the lower chamber as well as in the upper chamber and syringe, a time-consuming procedure which may not be performed with confidence that there will be no loss.

A variety of evacuators have been devised to overcome these disadvantages. A common approach is to provide the evacuator with a fluid-transmissive manifold having a pair of separate paths, one path for the fluid injected into the body cavity and one for the fluid removed. The debris-ladened fluid drained from the body cavity may either by separately collected, with new sterile fluid being supplied for lavage, as in U.S. Pat. No. 3,233,609, or it may be filtered and recycled, as in U.S. Pat. Nos. 1,925,230, and 3,892,226, among others.

It is clear that the first of these types of apparatus requires large reservoirs for the sterile fluid and the effluent, particularly if a substantial quantity of fluid is to be circulated through the body cavity being cleansed. This in turn requires the reservoirs be connected to the manifold by lengths of sterile flexible tubing if the surgeon is to easily manipulate the apparatus. Fluid circulation in such evacuators is generally gravity powered, and is controlled by the coordinated operation of a pair of manually operated valves, one between the manifold and the sterile fluid reservoir and the other between the manifold and the collection receptacle, although a syringe may be added (as indeed it is in U.S. Pat. No. 3,233,309) to provide alternate pressure and suction if desired. A disadvantage of this type of evacuator is in its complexity. Not only does it consist of a number of parts which must be assembled in sterile condition for use, but its very use is somewhat cumbersome, requiring as it does the sumultaneous manipulation of not only a catheter and a syringe, but also of several valves, the whole connected together and to various reservoirs by lengths of flexible tubing.

The second type of apparatus, by filtering and recirculating the initially sterile fluid, avoids a number of these problems. Since the fluid is recirculated, only small reservoirs are needed, and the entire unit may be hand held, as is the Ellik evacuator. As the fluid is circulated by the alternate compression and expansion of a syringe, flow control may be accomplished by a pair of automatically operated check valves arranged to provide unidirectional flow of fluid through the filter. Aside from the loss in performance that slow acting and/or jammed valves can produce, such apparatus is relatively complex, requiring the assembly of a number of parts, and is consequently difficult to clean during use and to sterilize if used more than once. Further, such evacuators are not as inexpensive as the Ellik evacuator if used only once.

OBJECTS OF THE INVENTION

Accordingly, it is an object of the present invention to provide an irrigation device for cyclically injecting and withdrawing initially sterile fluid from a body cavity, which device has provision for filtering cellular debris and other particulate matter from the effluent in order that the fluid may be reused, and yet which may be easily and positively manipulated.

Another object of the present invention is to provide such an irrigation device which has relatively few parts and consequently may be easily assembled and dissassembled for cleaning if desired.

Yet another object of the present invention is to provide such an irrigation device which is relatively inexpensive to manufacture.

A further object of the present invention is to provide an irrigation device in which the filtering or settling portion of the irrigation cycle may, if desired, be omitted so that rapid reversal of flow of fluid may be achieved in order to thoroughly agitate and better suspend particulate matter in a body cavity.

BRIEF SUMMARY OF THE INVENTION

These and other objects are met in the present invention of an irrigation device in which a single manually operable valve controls the path of fluid flow within a fluid transmissive manifold connecting together syringe, a sample collection receptacle, and a resectoscope or like device. The parts are so disposed that the device can easily be operated by both hands of the therapist, one hand holding the manifold and attached sample receptacle, the other, the syringe. The manifold is configured to incorporate a valve seat and a pair of directional ports, and includes the filter to remove particulate matter from the effluent withdrawn from the body cavity. The valve stem is hollow and fluid transmissive and communicates between the interior of the syringe and the selected directional valve port; it may be incorporated into the structure of the syringe. This configuration of valve seat and valve stem allows the directional valve to be operated by the relative motion between the syringe and the manifold. The sample collection receptacle may be a simple wide mouth jar configured to be threaded onto a mating section of the manifold. Thus the irrigation device may be fabricated as three simple parts: manifold, syringe and valve stem, and receptacle.

Other objects of the invention will in part be obvious and will in part appear hereinafter. The invention accordingly comprises the apparatus possessing characterisic features exemplified in the following detailed disclosure, the novel features of which are set forth in the appended claims.

BRIEF DESCRIPTION OF THE DRAWINGS

For a fuller understanding of the nature and objects of the present invention, reference should be had to the following detailed description taken in connection with the accompanying drawings wherein.

In all views, like numbers designate like parts.

DETAILED DESCRIPTION

Figure 1:
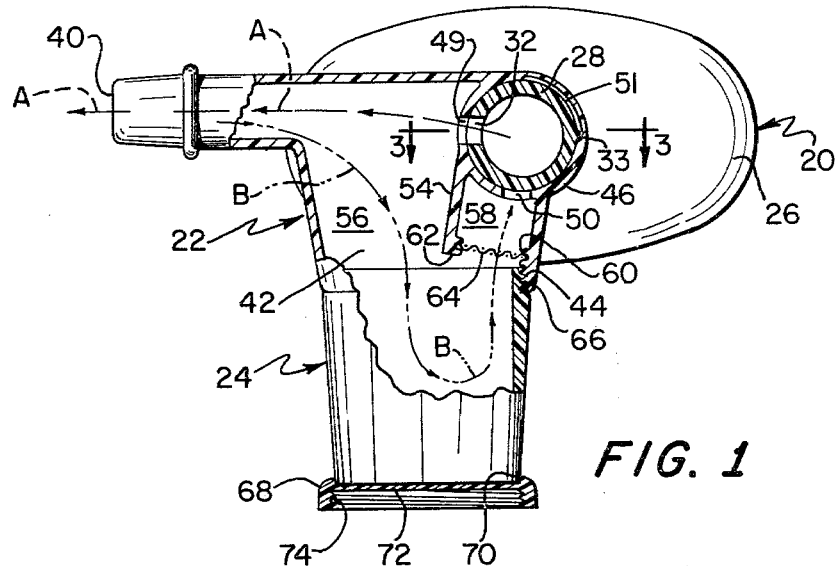
FIG. 1 is a side view, partially in section, of a preferred embodiment of the present invention, with the directional valve arranged to communicate between syringe 20 and manifold 22 by one of the fluid flow paths.

Referring to FIG. 1, there may be seen a medical, e.g. urological, irrigation device made in accordance with the principles of the present invention which in a preferred embodiment comprises a bulb-type syringe 20, a fluid transmissive manifold 22, and a collection receptacle 24. Syringe 20 may be of natural or synthetic rubber or similarly resiliently deformable material and manifold 22 and receptacle 24 may be of a relatively rigid impervious polymeric material, such as nylon or polysulfone, or alternately of glass or metal. All materials are futher chosen on the basis of chemical and biological inertness and compatability with the chosen method of sterilization (i.e., gas, autoclave, etc.). The device is dimensioned such that syringe 20 may be held and manipulated with one hand while manifold 22 and receptacle 24 are held in the other.

Syringe 20 comprises a hollow bulb 26 communicating with a hollow stem 28. In a preferred embodiment bulb 26 and stem 28 are of unitary construction, being molded as a single piece, with the walls of the stem being so dimensioned as to be thicker, and therefore more rigid, than those of the bulb, which is intended to be resiliently compressible. It will be understood, however, that bulb 26 and stem 28 could be individually fabricated and then joined together, as by a tight elastic friction fit, by an appropriate adhesive, or otherwise. Preferably bulb 26 is ovate with minor axes dimensioned to fit within the palm of a partly closed hand.

Figure 3:
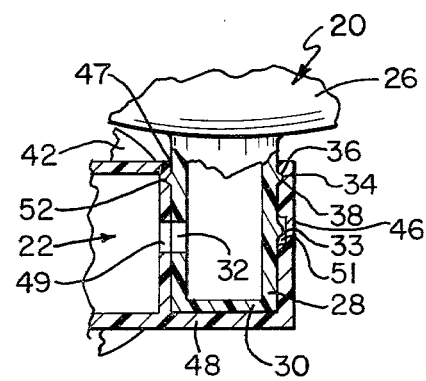
FIG. 3 is a partial sectional view, taken along the line 3—3 of FIG. 1, showing the method of attachment between syringe 20 and manifold 22.

Stem 28 is of right circular cylindrical form and is disposed substantially coaxially about the extension of a minor axis of bulb 26. The hollow interior of stem 28 communicates with the interior of bulb 26, and the end of the stem distal from the bulb is sealed off with a circular end cap 30, shown in FIG. 3. A portion of the cylindrical wall of stem 28 is pierced near end cap 30, thereby forming a radial aperture 32 through which the interior of bulb 26 and stem 28 can communicate with the exterior. In a preferred embodiment the line joining aperture 32 to the axis of stem 28 is made substantially parallel to the long axis of bulb 26. Diametrically opposite aperture 32, is a small pin 33. Pin 33 extends axially and radially a slight amount and is axially terminated with rounded ends. A circumferential ring 34 of slight axial and radial extent is provided encircling stem 28 between aperture 32 and bulb 26. Preferably, ring 34 is of triangular cross-section, one side of the triangle coinciding with the exterior of stem 28 and the other two sides delimiting beveled face 36 and 38 facing respectively toward and away from bulb 26.

Considering again FIG. 1, it may be seen that manifold 22 is in the general form of a thin walled elbow-shaped hollow conduit having straight arm segments 40 and 42 terminating in open ends adapted to secure and communicate with the interiors of a cannula, such as a resectoscope, (not shown) and collection receptacle 24, respectively. Toward this end, arm segment 40 is in the form of a relatively long narrow cylinder while arm segment 42 is a relatively short wide cylinder. Further, the open end of arm segment 42 is provided with internal threads 44.

Situated at the exterior bend of the elbow of manifold 22, and in part integral with the wall of the manifold, is cross conduit 46. Cross conduit 46 is of right circular cylindrical form and is disposed with its axis substantially orthogonal to the axes of arm segments 40 and 42. Cross conduit 46 is of hollow thin walled construction and has an inside diameter substantially the same as the outside diameter of stem 28. As may be seen with reference to FIG. 3, cross conduit 46 is provided with an open end 47, the other end being closed off by wall segment 48 which in a preferred embodiment is an extension of the thin wall of manifold. As will be explained hereinafter, receptacle 24 and manifold 22 of the preferred embodiment are intended to be held by the left hand, while syringe 20 is grasped by the right. Consequently, as seen from the open end of arm segment 40, with arm segment 42 lowermost, open end 47 is to the left and wall segment 48 is to the right.

Refering again to FIG. 1, it may be seen that cross conduit 46 is further provided with a pair of radial apertures 49 and 50 communicating between the interior of the cross conduit and the interior of manifold 22.

As seen from the axis of cross conduit 46, aperture 49 is in the direction of the open end of arm segment 40 of manifold 22 and aperture 50 is in the direction of the open end of arm segment 42. Apertures 49 and 50 are each of similar dimension as aperture 32 in stem 28, and they are spaced apart by at least the circumferential extent of a single aperture. Apertures 49 and 50 are spaced from wall segment 48 an amount similar to the distance between aperture 32 and end cap 30 of stem 28. Wall 46 is internally relieved with recess 51 dimensioned to receive pin 33 over a circumferential arc extending from diametrically opposite aperture 49 to diametrically opposite aperture 50. Cross conduit 22 is further provided with an internal circumferential notch 52, shown in FIG. 3, dimensioned to accept ring 34 of stem 28 and spaced from the interior of wall segment 40 a similar distance as ring 34 is from the exterior of end cap 30.

Refering again to FIG. 1, it may be seen that manifold 22 is provided with a partition 54 connected to the exterior of cross conduit 22 between apertures 49 and 50 and extending into arm segment 42 to a position just short of internal threads 44, so as to divided the arm segment into a pair of open ended chambers 56 and 58, respectively communicating directly with arm segment 40 (and including aperture 49) and with aperture 50. The open end of chamber 58 distal from aperture 50 is provided with a pair of closely spaced internal lips 60 and 62 defining between them a grove which retains filter screen 64. Filter screen 64 may be of plastic or wire mesh or other suitable material, and may either be molded in place in the fabrication of manifold 22 or inserted later. It will be understood the mesh of filter screen 64 is chosen on the basis of the size of the particulate matter to be removed by the screen, and if it is sufficiently large, the filter can be unitary with the structure of manifold 22.

Collection receptacle 24 is a wide-mouth jar dimensioned to be conveniently and firmly grasped by one hand and provided with external threads 66 dimensioned and configured to engage threads 44 of manifold 22. As an aid to handling, receptacle 24 is provided with a slight taper top to bottom, and as an aid to stability when placed on a surface, the receptacle is provided with an enlarged base 68. In a preferred embodiment, base 68 is detachable from collection receptacle 24, and comprises a short cylindrical body provided with a recess 70 and a threaded recess 74 disposed coaxially and separated by a thin wall 72. Recess 70 is dimensioned to tightly and resiliently fit the bottom of collection receptacle 24 and threaded recess 74 is configured to engage threads 66 of the receptacle.

The assembly of the major components of the irrigation device is simple. Stem 28 of syringe 20 is inserted into the open end 47 of cross conduit 46, and end cap 30 is forced toward wall segment 48. When pin 33 comes in contact with cross conduit 46, its rounded end cooperates with the cross conduit to resiliently distort stem 28 inward, allowing the pin to enter the cross conduit. As the end cap further approaches the wall segment, beveled face 38 of ring 34 contacts the interior of cross conduit 46, and stem 28 adjacent the ring resiliently distorts inwardly, allowing ring 34 to enter the cross conduit as well. When pin 33 and ring 34 come opposite recess 51 and notch 52, respectively, just as end cap 30 comes into contact with wall segment 48, the inward force exerted on the pin and the ring by cross conduit 46 is relieved, and elastic restoring forces urge the ring into the notch and the pin into the recess, thereby captivating stem 28 in the cross conduit in such a way that the stem and cross conduit may be rotated about their common axis by the angular extent of recess 51, but may only be axially moved apart by the exertion of sufficient force to distort the stem. Receptacle 24 is attached to manifold 22 by the cooperative engagement of threads 44 and 66.

It will be appreciated that the device is adapted to being individually packaged, either assembled or as separate components, in a sterile ready to use condition, and that during or after use the device may be disassembled to recover a sample of the particulate matter collected or to clean filter screen 64, by unscrewing receptacle 24 from manifold 22, or for thorough cleaning by further removing syringe 20 from the assembly. This may be accomplished by pulling bulb 26 away from manifold 22, exerting sufficient force to resiliently distort stem 28 through the interaction of beveled face 36 with notch 52. While the apparatus may be easily cleaned and sterilized for reuse, it will be noticed that it is of such simple construction as to be relatively inexpensive, and therefore may be treated as a disposable item after use.

Figure 2:
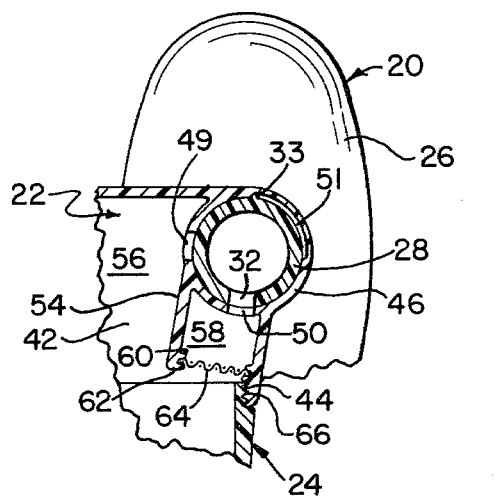
FIG. 2 is a fragmentary view, in section, similar to FIG. 1 but showing the directional value arranged to communicate between syringe 20 and manifold 22 by the alternate fluid flow path.

The operation of the device will now be briefly described. The assembled unit is connected, through the attachment at the open end of arm segment 40, with a resectoscope or other cannula and the entire device is filled with an appropriate sterile fluid. The embodiment illustrated is for use with the right hand operating syringe 20 and the left hand holding receptacle 24 and manifold 22. Bulb 26 is grasped between the fingers and thumb of the right hand with its long axis directed along the width of the palm. The bulb is compressed and released by the combined action of fingers and thumb, and the bulb and its attached stem 28 may be rotated by a simple wrist motion. Stem 28 and cross conduit 46 form, in effect, the stem and seat respectively of a directional valve which may direct the flow to and from syringe 20 either directly through chamber 56 or via chamber 58. Aperture 32 is aligned with aperture 49 by rotating bulb 26 until the major axis of the ovate bulb is substantially parallel with arm segment 40. With this arrangement of apertures, it will be noted that syringe 20 communicates directly with chamber 56 of manifold 22, and compression bulb 26 will force fluid from the bulb, through arm segment 40, and into the attached (but not illustrated) resectoscope along the path indicated by the dashed arrows A of FIG. 1. A quarter turn of bulb 26 counterclockwise as seen in the Figures results in the alignment of apertures 32 and 50, as shown in FIG. 2. Bulb 26 now communicates with chamber 58. This same action, of course, closes off aperture 49, which is now opposite a portion of the wall of stem 28. Relaxing the compressional forces on bulb 26 will now permit the bulb to expand, drawing fluid into the syringe through chamber 56, filter screen 64, and chamber 58, along the path indicated by the double dashed arrows B of FIG. 1. The extent of partition 54 insures that this path followed by the effluent departs markedly from the path A followed by the fluid being injected through aperture 49, the circuitous path B carrying debris in the effluent initially downward into receptacle 24. Pin 33, cooperating with the circumferential ends of recess 51, limits the rotation of stem 28 to insure alignment of aperture 32 with either aperture 49 or 50 at the rotational extremes.

Filter screen 64 prevents the flow of particulate matter into syringe 20, and the initially downward flow of effluent facilitates collection of debris in receptacle 24. If laboratory examination of a particulate sample is desired, collection receptacle 24 may be unscrewed from manifold 22, and base 68 removed from the bottom of the receptacle and used as a sealing cap, being attached to the top of the receptacle by threaded recess 74.

It should be noted that the directional valve formed by stem 28 and cross conduit 46 need not be alternated between each compression and expansion of bulb 26. This feature is of advantage when it is desired to provide particularly vigorous agitation, as for instance to initially place in suspension particulate matter in the body cavity being cleansed or to clear a blockage in the resectoscope, both of which may best be accomplished by rapidly compressing and expanding bulb 26 with aperture 32 opposite aperture 49. Then again, this feature may be used to clean accumulated debris off filter screen 64 be occassionally compressing bulb 26 while aperture 32 is aligned with aperture 50.

It will be understood that various changes may be made in the apparatus described without departure from the principles of the invention. For instance, the device can be made "left handed" by interchanging the positions of open end 47 and wall segment 48. Then again, bulb 26 may be of other shape than ovate (e.g., spherical), and, indeed, syringe 20 could even be a piston syringe with thumb and finger rings. Further, stem 28 could be provided with a plurality of apertures so that commutation between apertures 49 and 50 in cross conduit 46 need not entail the rotation of an individual aperture in the stem between the two apertures, or it could be made to rotate independently of any motion of the syringe, being controlled for instance by a thumb-activated lever. Alternatively, syringe 20 may be held captive to manifold 22 by a threaded flange and nut, such as in a common plumbing union, by resiliently distortable O-rings, or the like, rather than by ring 34 and notch 52. Also, partition 56 could be extended to contact the top of receptacle 24, and filter screen 64 could be incorporated into the receptacle to cover a segment of its top. Accordingly, it is intended that all matter contained in the above description and shown in the accompanying drawings shall be interpreted as illustrative and not in a limiting sense.

What is claimed is:

1. A medical irrigation device for alternately introducing fluid into and withdrawing fluid from a body cavity through a cannula, said device comprising in combination:

a fluid receptive manually operable syringe;
a specimen collecting receptacle;
a fluid conductive manifold including a fluid conductive first arm segment, and a bifurcated fluid conductive second arm segment connected substantially orthogonally thereto, said first arm segment including means for providing connection to and establishing open communication with said cannula, and said second arm segment including means for providing connection to and establishing open communication with said specimen collecting receptacle; said second arm segment comprising a first fluid conduit and a second fluid conduit, said first fluid conduit being between and in open communication with said first arm segment and said specimen collecting receptacle and said second fluid conduit communicating with said specimen collecting receptacle through a particulate filter means; and
a manually operable valve means for controllably establishing open communication alternatively between said syringe and said first arm segment and between said syringe and said second fluid conduit.

2. A device according to claim 1 wherein said manually operable valve means comprises a radially symmetrical fluid conductive stem and a mating hollow valve seat in which said stem may be manually rotated about its axis of symmetry, said stem being attached to and in open communication with said syringe and further having at least one radially disposed aperture through which fluid may be transported into and out of said syringe, and said valve seat having a radially disposed first port in communication with said first arm segment and a radially disposed second port in communication with said second fluid conduit, said first port and said second port being additionally so disposed as to alternately be in opposition to and communication with a one of said apertures.

3. A device according to claim 2 wherein said stem may be rotated relative to said valve seat by the rotation of said syringe relative to said manifold.

4. A device according to claim 3 wherein said axis of symmetry of said stem is disposed substantially orthogonal to said first arm segment and said second arm segment.

5. A device according to claim 4 wherein said syringe is a manually compressible bulb.

* * * * *